United States Patent [19]
Fratantoni et al.

[11] Patent Number: 5,325,295
[45] Date of Patent: Jun. 28, 1994

[54] ADAPTATION OF MICROTITER PLATE TECHNOLOGY TO MEASUREMENT OF PLATELET AGGREGATION

[75] Inventors: Joseph C. Fratantoni, Rockville; Betty J. Poindexter, Kensington, both of Md.

[73] Assignee: The United States of America as represented by the Secretary of the Department of Health and Human Services, Washington, D.C.

[21] Appl. No.: 688,220

[22] Filed: Apr. 22, 1991

Related U.S. Application Data

[63] Continuation-in-part of Ser. No. 347,087, May 4, 1989, abandoned.

[51] Int. Cl.$^5$ .................. G06F 15/00; G01N 33/48
[52] U.S. Cl. ................ 364/413.08; 364/413.07; 356/39; 356/426; 356/427; 422/69; 422/73
[58] Field of Search .................. 364/413.08, 413.07; 356/39, 426, 427; 422/69, 73

[56] References Cited

U.S. PATENT DOCUMENTS 4,580,895  4/1986  Patel .................................. 356/39

OTHER PUBLICATIONS

Platelet Function Testing, proceedings from Workshop on Platelets: "The Significance of Platelet Function Tests in the Evaluation of Hemostatic and Thrombotic Tendencies", Philadelphia, PA., Oct. 18–19, 1976.

*Primary Examiner*—Roy N. Envall, Jr.
*Assistant Examiner*—Gita D. Shingala
*Attorney, Agent, or Firm*—Lowe, Price, LeBlanc & Becker

[57] ABSTRACT

A rapid method for the simultaneous measurement of aggregation or agglutination in plurality of microtest wells or other sample-holding vessels comprises providing a plurality of light beams having discrete focal points adapted to be focused on the contents of a plurality of wells or other vessels and a plurality of photodetectors therefor, directing the light beams through the wells or other vessels and contents thereof, continuously agitating the wells or other vessels and contents thereof with a circular movement effective to permit aggregation or agglutination while preserving the integrity of the material, producing a plurality of output signals from the detectors are proportional to the light absorbencies of the beams as they pass through the wells or other vessels and contents thereof, repeatedly sampling the signals at a predetermined time interval and determining changes in optical densities from the signals obtained after each predetermined time interval by comparing each signal sampled after each predetermined time interval with the first signal sampled for the same microtest well or vessel, whereby any change in optical density which is greater than about 0.05 units is said to indicate that aggregation or agglutination occurred in the well or other vessel. The present method is suitably applied to the measurement of aggregation in platelets.

20 Claims, 3 Drawing Sheets

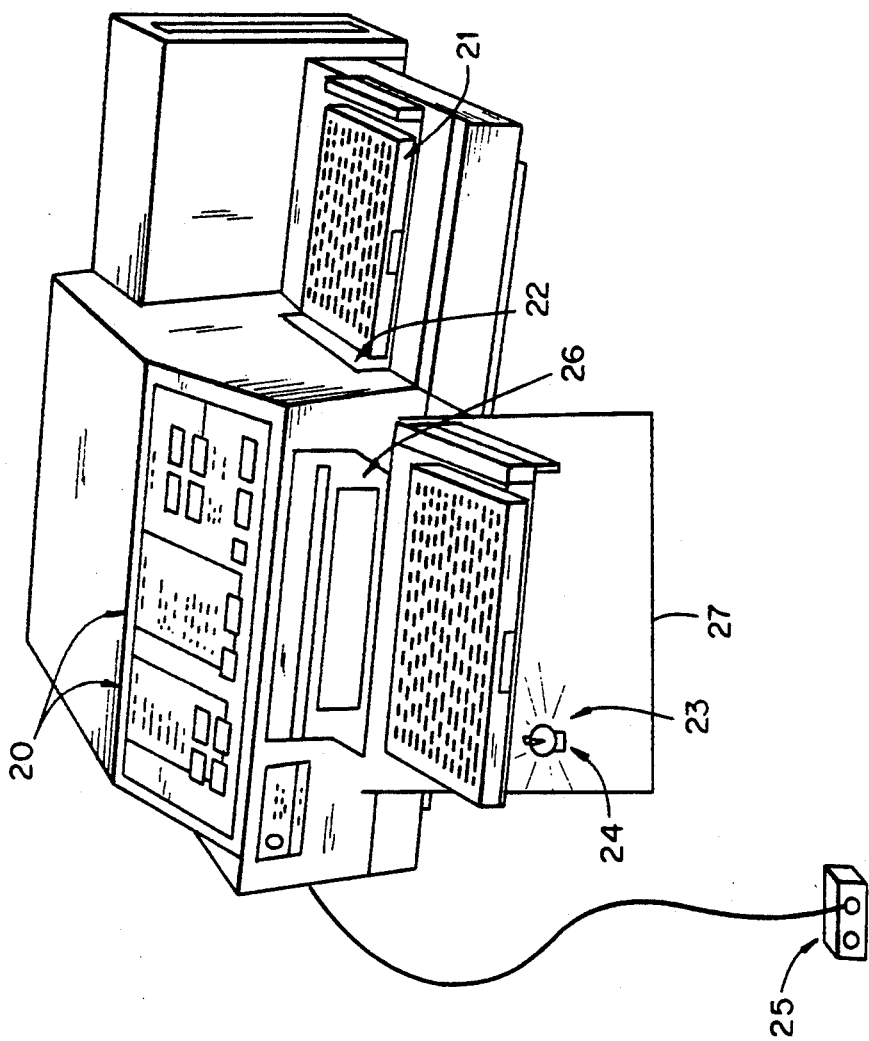

ADAPTATION OF MICROTITER PLATE TECHNOLOGY TO MEASUREMENT OF PLATELET AGGREGATION

TECHNICAL FIELD

This application is a continuation in part of application Ser. No. 07/347,087, filed May 4, 1989 now abandoned.

This invention relates to a new technical approach to aggregation measurements. The present method permits the simultaneous measurement of a large number of samples within a brief period of time and it provides output data in a form which is easily stored and immediately available for computer-assisted analyses. The method is time-saving, utilizes cutting edge technology and provides accurate results in a substantially inexpensive manner. It heavily relies on the simultaneous detection of transmitted light for up to 96 samples and requires a predetermined agitation mode, and optionally a somewhat constant temperature. Thus, the method is useful for the determination of aggregation in samples of unknown components. In a particular embodiment of the invention the method applies to the determination of platelet aggregation by a variety of aggregating agents.

BACKGROUND ART

Since 1962, light transmission measurements have been utilized to detect aggregation caused by a variety of agents (Born, G. V. R., J. Physiol. 162:67P (1962)); Born, G. V. R., Nature 194:927 (1962)). In a matter of seconds after the addition of an aggregating agent it is observed a large increase in light transmission associated with the formation of aggregates. After a short but variable time, the light transmission may either decrease again indicating the dispersion of the aggregates, or increase even further. The latter is caused by an increase in the distance between the aggregates (Born G. V. R., and Hugh, M., Nature 215:1027 (1967)). The changes in transmitted light have been given a mathematical treatment based on a series of assumptions relating to the manner in which aggregation occurs (Cronberg, S., Coagulation 3:139 (1970)).

In the case of platelet aggregation, considerable evidence suggesting that adenosine diphosphate (ADP) plays an essential role (Michael, S., and Firkin, B. G., Ann Rev. Pharmacol. 9:95 (1969); Mustered, J. F., and Packham, M. A., Pharmacol. Rev. 22:97 (1970)). ADP, whether added or formed in the platelets, has been shown to cause the initial transformation in platelet morphology preceding aggregation. Ethylenediaminetetraacetate (EDTA) was added in concentrations sufficient to prevent aggregation and the plasma was then diluted to decrease the platelet concentration. It was found that the decrease in light transmission is only associated with the change and shape of the platelet and not with an increase in the main volume of the cells (Zucker, M. B., and Zaccardi, J. B., Fed. Proc. 23:299 (1964)).

The measurement of aggregation in a sample is of fundamental importance in studies of, e.g., platelet behavior. The basic technique for the measurement of aggregation utilizes changes in optical transmission of readings. Data collection was completed within 10 a suspension of aggregatable particles or material, e.g., platelets, as it is converted into a suspension of aggregates, and records these changes with a spectrophotometer fitted with, e.g., a magnetic stirrer, a thermostatted cuvette and a chart recorder. (Mustard, J. F. and Packham, M. A., Pharmacol Rev 22:97–187 (1970)).

Typically, most instruments detect the formation of aggregates by monitoring either optical turbidity or electrical conductivity. The latter represents the traditional approach employed by a so-called fibrometer-type instrument. In fact, this instrument measures increases in conductivity which may be correlated to the formation of aggregates. Similarly, turbidity may be optically sensed by the decrease in light transmission due to the formation of aggregates.

Some optical instruments permit two or four samples to be run and the results are recorded simultaneously. Other new devices allow for the electronic storage of aggregation curves. Up to the present time the applications of aggregation measurements have been restricted because of the variation between samples, the limited stability of suspensions and the cumbersome nature of individual tracings. Aggregation data are commonly reported for publication as subsequent tracings done on a single sample. These tracings are often accompanied by a footnote indicating that the data presented are representative of a number of similar experiments.

Various photometers are commercially available for measuring the light absorbance of liquid samples in microtitration plates or other sample-holding vessels. Example of such equipment are the MR 600 Microplate Reader marketed by Dynatech Laboratories, Inc. of Alexandria, Va., and the Vmax Kinetic Microplate Reader marketed by Molecular Devices of Palo Alto, Calif.

Born, G. V. R, Nature 4832:927 (1962) utilizes large volume samples (3 ml samples) contained in a centrifuge tube, the content of the tube is stirred gently with a rod and the optical density of each sample is individually measured. It is reported in this article that vigorous stirring at 1,000 rpm cycles/minute contribute to the breaking up of platelets.

Michal, F., and Born, G. V. R., Nature New Biol. 231:220 (1971) disclose a modification of the traditional optical method of measuring aggregation which permits the simultaneous measurement of scattered and transmitted light. This method encompasses a modification of the cuvette chamber of an aggregometer to allow for the measurement of light scattered at right angles to the incident light beam. In the aggregometer the incident light beams a suspension of platelets which are kept in rapid motion by a magnet rotating in the bottom of the glass tube at 1,000 rpm. The sample volume is about 1 ml and the optical density is read individually for each sample which is kept in a water-jacketed environment at 37° C.

Mills, D. C. B., and Roberts, G. C. K., J. Physiol. 193:443–453 (1967) measure platelet aggregation in a modified EEL Long Cell Absorptiometer manufactured by Evans Electro-selenium Ltd., of Halstead Essex the measurements are taken of a plasma sample which is stirred from below by a magnetic stirrer while continuous recordings are made. The volume sample is about 1.0 ml. O'Brien, J. R., Nature 202:1188 (1964) conduct aggregation studies of 2 ml plasma samples placed in a cuvette in an EEL titrometer or electrophotometer. Each sample is treated individually and it is said that aggregation occurs when the optical transmission increases and is continuously recorded downwardly on the tracings.

O'Brien, J. R., J. Clin. Path. 15:446 (1962) observed the adherence of blood platelets to glass by depositing samples on a glass slide and covered it with a cover slip. The method of detection is by microscope and the viscous metamorphosis or platelet aggregation is observed. This method also utilizes large samples which are placed in glass tubes.

In recent years, microtiterplates (MP) have been increasingly used in a number of analytical applications. These disposable plastic plates contain 96 wells with a working volume of 0.3 ml per well. The wells are positioned in 12 by 8 array. Spectrophotometric devices which interface with microcomputers are commercially available which permit the rapid reading of optical changes occurring in the wells. Moreover, the thus obtained data may be electronically stored in a computer memory.

However, up to the present time there has not been available an apparatus or method for obtaining simultaneous spectrophotometric readings for a plurality of samples and controls utilizing efficient agitation, and optionally temperature conditions to follow aggregation, which could then be mathematically treated and averaged, including by computer technology, to provide statistically significant results.

SUMMARY OF THE INVENTION

This invention relates to a rapid method for the simultaneous measurement of aggregation, or agglutination of a material in a plurality of microtest wells or other sample-holding vessels, the method comprising providing a plurality of light beams having discrete focal points adapted to be focused on the contents of a plurality of wells or other vessels and a plurality of photodetectors therefor;

directing the light beams through the wells or other vessels and contents thereof;

continuously agitating the wells or other vessels and contents thereof with a circular movement effective to permit aggregation or agglutination while preserving the integrity of the material;

producing a plurality of output signals from the detectors which are proportional to the light absorbencies of the beams as they pass through the wells or other vessels and contents thereof;

repeatedly sampling the signals at a predetermined time interval; and determining changes in optical densities from the signals obtained after each predetermined time interval by comparing each signal sampled after each predetermined time interval with the first signal sampled for the same microtest well or vessel, whereby each change in optical density which is greater than about 0.05 units is said to indicate that aggregation or agglutination occurred in the well or other vessel.

Also disclosed herein is a novel method which is an improvement over prior art methods for measuring aggregation or agglutination of a material by determining changes in optical density of the content of a sample, the improvement comprising providing a plurality of light beams having discrete focal points adapted to be focused on the contents of a plurality of wells or other vessels and, a plurality of photodetectors therefor;

directing the light beams through the wells or other vessels and contents thereof;

continuously agitating the wells or other vessels and contents thereof with a circular movement effective to permit aggregation or agglutination while preserving the integrity of the material;

producing a plurality of output signals from the detectors which are proportional to the light absorbencies of the beams as they pass through the wells or other vessels and contents thereof;

repeatedly sampling the signals at a predetermined time interval; and determining changes in optical densities from the signals obtained after each time interval by comparing each signal sampled after each predetermined time interval with the first signal sampled for the same microtest well or other vessel, whereby each change in optical density which is greater than about 0.05 units is said to indicate that aggregation or agglutination occurred in the well or other vessel.

A more complete appreciation of the invention and many of the attendant advantages thereof will be readily perceived as the same becomes better understood by reference to the following detailed description when considered in connection with the accompanying figures.

BRIEF DESCRIPTION OF DRAWINGS

FIGS. 2–4 show prior art devices useful in practicing aggregation or agglutination testing.

DETAILED DESCRIPTION OF THE DRAWINGS

Figure 1:
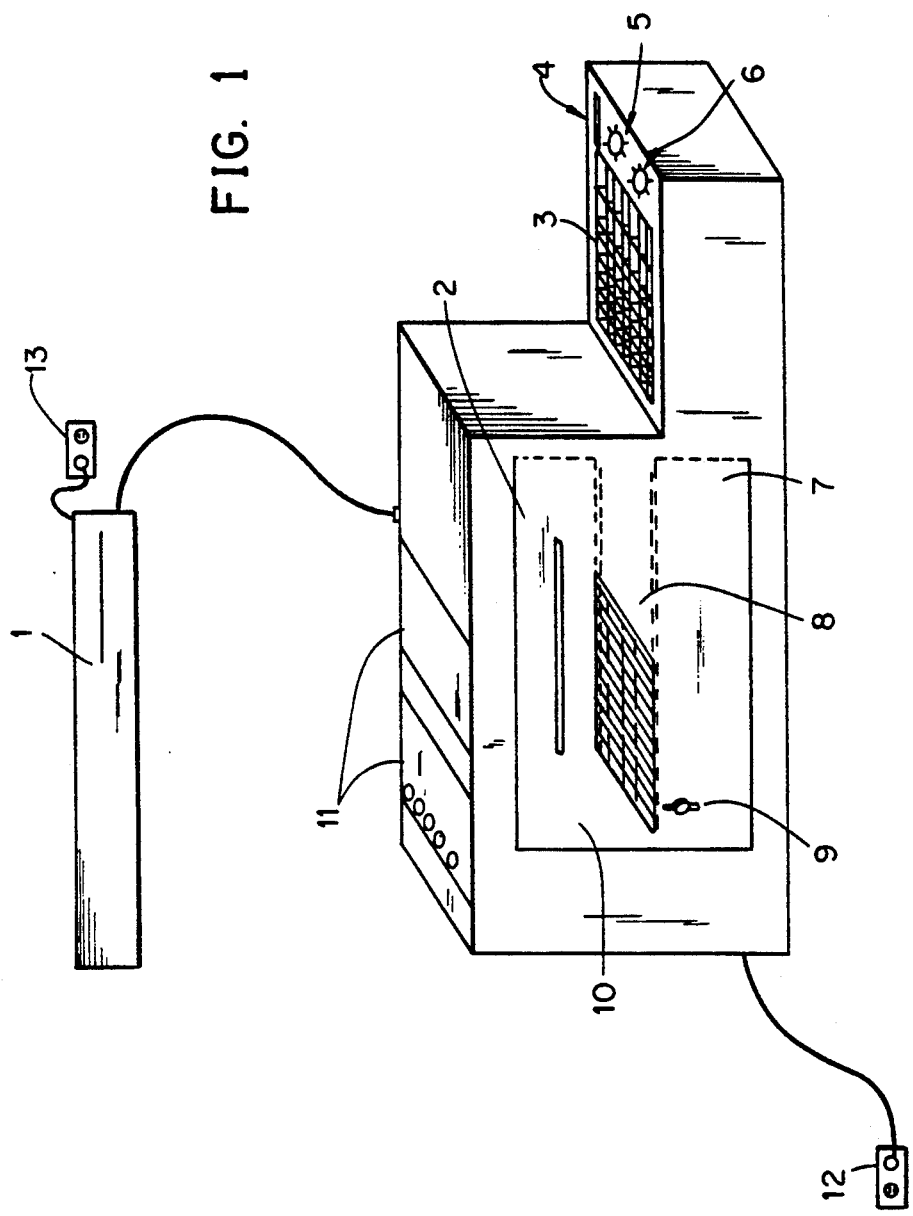
FIG. 1 shows a device which may be used in practicing the method of the present invention.

FIG. 1 is described as follows. Item number 1 represents a computer for data collection and analysis which is attached to the rest of the device by communication devices; item 2 represents a photocollector capable of rapidly collecting output from multiple wells within seconds; item number 3 represents a microplate with multiple sample ells (96 maximum); item number 4 represents an on/off switch for the device to activate agitation; item 5 represents an agitation control switch to regulate agitation to specific rates (950–1600 rpm, for example); item number 6 represents a timing device for regulating the amounts of time the microplate is subjected to agitation; item number 7 represents a cut-away view of the photometer chamber; item number 8 represents a track capable of moving the microplate from the shaker portion of the device into the read position of the photometer and back out to the agitation site; item number 9 represents a light source capable of scanning multiple wells within seconds; item number 10 represents the photometer chamber; item number 11 represents the photometer controls, the wavelength read mode; and item number 12 represents an electrical power source for supplying power to run the device.

Figure 4:
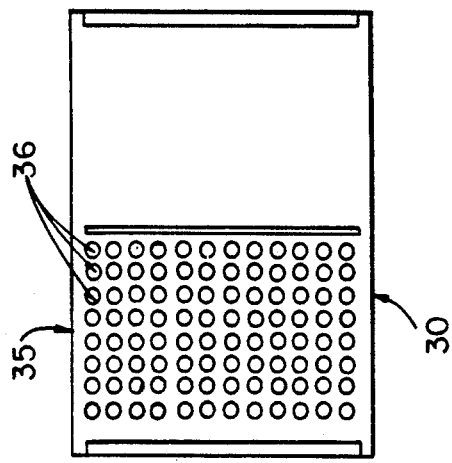
Figure 3:
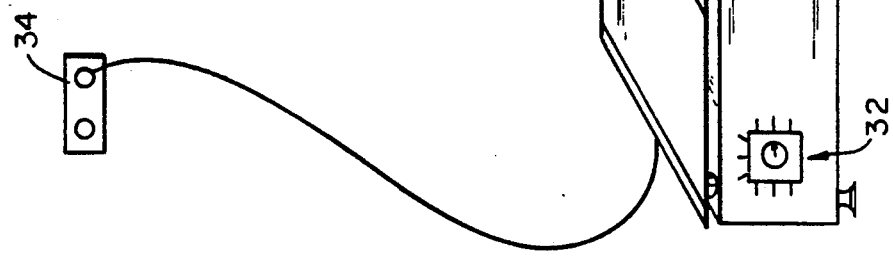

FIGS. 2–4 relate to general illustrations of prior art devices useful in a process for measuring aggregation and agglutination of material in a plurality of microtest wells or for preparing the samples by agitating the samples for such tests.

FIG. 2 relates to a general illustration of a $V_{max}$ Kinetic Microplate Reader. The essential aspects of this device are as follows: Item number 20 represents photometer controls, item number 21 illustrates a microplate for holding samples, item number 22 represents a photometer chamber, item number 23 represents a device attached to a light source capable of rapidly scanning multiple wells within seconds, item 24 relates to the light source itself, item number 25 relates to an electrical source for supplying power for time Vmax Kinetic Microplate Reader, item number 26 relates to a photocollector capable of rapidly collecting output from multiple wells within seconds and item number 27 represents the photometer chamber, as depicted by a cut-away view in this portion of the illustrative drawing.

FIG. 3 relates to a general illustration of a Dynatech Minishaker agitating device. Item number 30 represents a plate agitation site on the device, item number 31 represents an on/off switch to control the minishaker when in use, item number 32 represents agitation control wherein each setting on the minishaker has the number of cycles per minute determined, item number 33 represents a timing device attached to the shaker for determining the length of time the microplate is subjected to agitation on the minishaker and item number 34 represents a power source for running the minishaker.

FIG. 4 represents an overhead view of the minishaker agitating surface. Item number 30 represents the plate agitation site, item number 35 represents the microplate sitting upon the plate agitation site and item number 36 represents the multiple sample wells (96 maximum) of the microplate which is sitting on the plate agitation site.

As can be seen from FIGS. 2-4 the plate reading device is separate from the plate agitation device.

Other objects, advantages and features of the present invention will become apparent to those skilled in the art from the following discussion.

BEST MODE FOR CARRYING OUT THE INVENTION

This invention arose from a desire by the inventors to improve on prior art technology suitable for the measurement of aggregation or agglutination by simultaneously determining changes in optical densities of the contents of a plurality of samples. More particularly, the present method can be applied to the measurement of platelet aggregation as well as the aggregation of other macromolecules or biological components. The present method relies on known technology for the simultaneous reading of multiple samples. This method improves thereupon by providing, inter alia, particular steps and conditions which contribute to unexpectedly improved results in terms of greater accuracy and reliability of the results obtained.

The present method provides for the advantageous simultaneous reading of a large number of samples within a brief period of time by controlling the agitation conditions, and optionally the temperature environment, and results in output data which can be readily stored and immediately recalled for computer-assisted analysis.

This invention thus provides a rapid method for the simultaneous measurement of aggregation or agglutination of a material in a plurality of microtest wells or other sample-holding vessels, the method comprising providing a plurality of light beams having discrete focal points adapted to be focused on the contents of a plurality of wells or other vessels and a plurality of photodetectors therefor;

directing the light beams through the wells or other vessels and contents thereof;

continuously agitating the wells or other vessels and contents thereof with a circular movement effective to permit aggregation or agglutination while preserving the integrity of the material;

producing a plurality of output signals from the detectors which are proportional to the light absorbencies of the beams as they pass through the wells or other vessels and contents thereof;

repeatedly sampling the signals at a predetermined time interval; and determining changes in optical densities from the signals obtained after each predetermined time interval by comparing each signal sampled after each predetermined time interval with the first signal sampled for the same microtest well or vessel, whereby each change in optical density which is greater than about 0.05 units is said to indicate that aggregation or agglutination occurred in the well or other vessel.

The device shown by FIG. 1 may be efficiently and easily used to practice the method according to the present invention. Other devices will be readily apparent to one of ordinary skill in the art upon consideration of the illustrated example device.

In general, the present method is preferably conducted at a temperature of about 15°-37° C., more preferably about 20°-37° C., and still more preferably at room temperature or about 20°-25° C. However, any temperature not damaging the components and permitting for aggregation to occur can be utilized herein. Most typically, the method is practiced at room temperature.

Still more preferred for the practice of the method of the invention is to continuously agitate the wells or other vessels with a circular movement having a diameter of about 1.1-1.5 mm, more preferably about 1.2-1.4 mm, and still more preferably about 1.25-1.35 mm. Also, preferred are frequencies of agitation of about 970-1800 cycles/min., more preferred about 970-1,600 cycles/min, and still more preferred about 970-1,350 cycles/min. In general, below about 950 cycles/min aggregation does not appear to occur at room temperature. However, under other conditions of temperature frequencies of less than 970 or 950 cycles/min may also be utilized.

In still a more preferred embodiment of the method it is considered that agglutination or aggregation has occurred if the change in optical density is greater than about 0.1, and still more preferred greater than about 0.8 units.

In a particular embodiment of the invention the microtest wells or other vessels contain a liquid medium selected from the group consisting of a substantially light-transparent liquid medium, a liquid sample comprising an agglutinatable or aggregatable material, a liquid sample comprising an agglutinatable or aggregatable material and an agglutinating or aggregating agent, an agglutinatable or aggregatable material-rich liquid medium and an agglutinatable or aggregatable material-poor liquid medium.

That is, any medium or sample can be tested for the presence of an agglutinatable or aggregatable material by adding an agglutinating or aggregating agent and conducting the various steps enumerated by the present method. Other media can be also utilized in the microtest wells or other vessels such as a control which may be a regular liquid medium such as a buffer, an agglutinatable or aggregatable material-rich liquid medium such as platelet rich plasma or platelets centrifuged from plasma and resuspended in another medium, an agglutinatable or aggregatable material-poor liquid medium such as plasma supernatant after centrifuging out platelets thereof, among others. Other media and samples may also be utilized for different applications as is known in the art.

These media and the results obtained for them by applying the present method can be utilized to normalize the samples, measurements and/or to set up parameters for a scale in relation to which all measurements will be calculated. In addition, a liquid medium containing pre-established amounts of aggregatable or agglutinatable material, and optionally additional agglutinating or aggregating agent, may also be subjected to the present method to thereby obtain standard curves, the points of which correspond to known amounts of aggregatable or agglutinatable material, e.g., platelets, in the samples.

The manner in which these controls and standard curve points are prepared and/or utilized for the analyses of the data is known in the art and need not be repeated herein in detail. (Triplett, D. A., (Ed)., "Platelet Function: Laboratory Evaluation and Clinical Application", Am. Soc. of Clinical Pathologists, Publisher, Chicago (1978)).

In a preferred aspect of the invention, the method is conducted at a substantially constant temperature. That is, it is not necessary to ensure the constancy of the temperature at, say, less than 0.1° C. It is, however, preferred that the temperature be maintained constant within about 2°–3° C., more preferably about 1°–2° C. In general, the method is conducted in a range of temperature which will not damage the materials being studied and which at the same time permit the occurrence of aggregation or agglutination.

In a particularly preferred embodiment of this invention the agglutinatable or aggregatable material comprises platelets. When the method of the invention is applied to the measurement of aggregation or agglutination of platelet-containing samples the agglutinating or aggregating agent can be selected from the group consisting of ADP, thrombin, collagen, arachidonic acid, epinephrine, and combinations of these, among others. Other agglutinating or aggregating agents are known in the art and can also be utilized within the confines of this invention. (Triplett, D. A., (Ed)., "Platelet Function: Laboratory Evaluation and Clinical Application", Am. Soc. of Clinical Pathologists, Publisher, Chicago (1978)).

In still another preferred embodiment of the invention, the method of the invention utilizes at least one microtest well or other vessel containing an agglutinatable or aggregatable material-poor liquid medium;

at least one microtest well or other vessel containing a similar but agglutinatable or aggregatable material-rich liquid medium; and at least one microtest well or other vessel containing a sample comprising an agglutinatable or aggregatable material; and said method further comprising adding to each microtest well or sample-holding vessel an agglutinating or aggregating amount of an agglutinating or aggregating agent prior to repeatedly sampling the plurality of signals at predetermined time intervals; and outputting into a computer the plurality of signals for each preset time and determining the optical density by further correcting each time signal for the optical density of the agglutinatable or aggregatable material-poor and material-rich media.

In this particular embodiment of the invention, an agglutinatable or aggregatable material-poor liquid medium and agglutinatable or aggregatable material-rich liquid medium are utilized along with the sample medium comprising the agglutinatable or aggregatable material.

In the context of this invention, an agglutinatable or aggregatable material-poor liquid medium can be defined as an aqueous solution with appropriate salt concentration and buffer capacity such that when and if platelets suspended in the medium retain their functional capacity for the duration of the procedure. An agglutinatable or aggregatable material-rich liquid medium is defined herein as a suspension of platelets in an appropriate medium such that the platelets retain their functional capacity, at a concentration which yields a low transmission of light through the medium which is appropriate for establishing the 0% transmission point of the scale. Typically, this is a concentration higher than normally encountered.

As already indicated above, the agglutinatable or aggregatable material-poor and agglutinatable or aggregatable material-rich liquid medium are utilized to establish a high and a low point in the scale of light transmission. All other measurements are thereafter related to these values as is known in the art. (Mustard, J. F., and Packham, M. A., Pharmacol. Rev 22:97–187 (1970)).

In the above method, after all the samples are prepared, to each microtest well or sample-holding vessel may be added an agglutinating or aggregating amount of an agglutinating or aggregating agent prior to repeatedly sampling the plurality of signals at predetermined time intervals. The plurality of signals obtained for each preset time is outputted into a computer and corrected optical densities is determined by further correcting each time signal for the optical density of the medium and its major components; that is, the agglutinatable or aggregatable material-poor and agglutinatable or aggregatable material-rich liquid media and their light transmissions. This can be done by a variety of manners known in the art. By means of example the percent transmission of a particular sample may be determined from the formula $$\% T_t = \frac{(OD_{MAt} - OD_{MPt})}{(OD_{MRt} - OD_{MPt})} \times 100$$

wherein
  $\%T_t$ is the percent transmission of light at time t;
  $OD_{MRt}$ is the optical density of the material-rich medium at time t;
  $OD_{MPt}$ is the optical density of the material poor medium at time t;
  $OD_{MAt}$ is the optical density of the medium comprising the material at time t; and
  $OD_{At}$ is the corrected optical density of the medium comprising the material.

In another preferred embodiment of the invention, the method further comprises averaging the changes in optical densities for the signals obtained for microtest wells or other vessels which contain the same medium or sample for the same time interval. This means that, when more than one microtest well or other vessel are loaded with the same unknown sample, namely the same concentration of sample, their values can be averaged and a standard deviation calculated by known methodology. (Glantz, S. A., Primer of Biostatistics, McGraw Hill, New York pp. 10–55 (1977)).

The fact that all the measurements are taken simultaneously and not at a later time from one another provides for an increased accuracy of the results, particularly because the waiting time, preparation and state of the samples, and the conditions under which the measurements are made are standardized and substantially the same.

Particularly preferred is the agitation of the samples in accordance with this invention when it is conducted continuously, and it is stopped immediately before producing each plurality of output signals. The agitation is then preferably restarted immediately thereafter. For all practical purposes the period during which the samples are not agitated in accordance with this invention may be substantially negligible when compared with the overall time incurred in the practice of the method. Typically, when the agitation is conducted at a separate sites from the spectrophotometric measurements the period during which the samples are not agitated may be as short as 5 seconds or less. With an apparatus having the capability for agitation required by the present method, the waiting time need not be greater than 1 second. In fact, present technology permits the reprogramming of existing software for controlling the agitation of samples in commercially available spectrophotometers to incorporate the agitation characteristics required by this method.

In a particularly useful embodiment of the invention, the method provides for the simultaneous measurement of aggregation or agglutination in a plurality of microtest wells or other sample-holding vessels comprising up to about 96 microtest wells or other vessels. Although not all the wells or vessels need be utilized, commercially available microtest plates contain 96 wells or vessels. Thus, up to this number of samples can be analyzed simultaneously in any one particular run. It is understood, however, that less than 96 samples may also be analyzed. In cases where a lesser number of samples is utilized for the practice of the present method the computerized software is reprogrammed in a manner such that it computes only the data from the wells or other vessels which are in fact being utilized.

With the advent of technology adapted for the measurement of larger numbers of separate signals obtained from a larger plurality of samples, it is contemplated that the present method be applied thereto. Accordingly, such variations including a larger or smaller number of simultaneously measured samples are considered to be within the confines of this invention.

Typically, when practicing the present method the determination of the changes in optical densities of the signals for each time interval or each cycle may be completed within less than about 1 minute. A sequence of about 10–12 cycles can be completed in about 5–10 minutes, and sometimes in a shorter period of time.

In a further preferred embodiment of the invention the method further comprises diluting the medium comprising the material in a further medium to obtain a plurality of samples comprising the further medium and the material at predetermined dilutions; and wherein a plurality of microtest wells or other vessels contain such samples comprising the further medium and the material at the predetermined dilutions.

It is understood that the above described improvement on the basic method of the invention can be applied to diluting unknown samples as well as to obtaining standard curves for different samples having known of predetermined amounts of agglutinatable or aggregatable material. In general, the dilutions are conducted by adding a predetermined amount of the same or a similar medium in which the material is present, and the dilution factors may be whole numbers; fractions thereof or multiples thereof. This means that the concentration of each successively diluted sample will be a predetermined fraction of the original concentration.

In another aspect of the invention, it is provided an improvement on a method for measuring aggregation or agglutination of a material by determining changes in optical density of the content of a sample, the improvement comprising providing a plurality of light beams having discrete focal points adapted to be focused on the contents of a plurality of wells or other vessels and, a plurality of photo detectors therefor;

directing the light beams through the wells or other vessels and contents thereof;

continuously agitating the wells or other vessels and contents thereof with a circular movement effective to permit aggregation or agglutination while preserving the integrity of the material;

producing a plurality of output signals from the detectors which are proportional to the light absorbencies of the beams as they pass through the wells or other vessels and contents thereof;

repeatedly sampling the signals at a predetermined time interval; and determining changes in optical densities from the signals obtained after each predetermined time interval by comparing each signal sampled after each time interval with the first signal sampled for the same microtest well or other vessel, whereby each change in optical density which is greater than about 0.05 units is said to indicate that aggregation or agglutination occurred in the well or other vessel.

In general, the present method if preferably conducted at a temperature of about 15°–45° C., more preferably about 20°–40° C., and still more preferably at room temperature or about 25°–35° C. However, any temperature not damaging the components and permitting for aggregation to occur can be utilized herein. Most typically, the method is practiced at room temperature.

Still more preferred for the practice of the method of the invention is to continuously agitate the wells or other vessels with a circular movement having a diameter of about 1.1–1.5 mm, more preferably about 1.2–1.4 mm, and still more preferably about 1.25–1.35 mm. Also, preferred are frequencies of agitation of about 970–1800 cycles/min., more preferred about 970–1,600 cycles/min, and still more preferred about 970–1,350 cycles/min. In general, below about 950 cycles/min aggregation does not appear to occur at room temperature. However, under other conditions of temperature frequencies of less than 970 or 950 cycles/min may also be utilized.

This invention provides a clear improvement over known methods for studying aggregation or agglutination of specific materials by observing changes in light transmission of suspensions while magnetically or manually stirring a sample comprising the material in a photometric cuvette. The present method provides the critical conditions for agitation of the samples, and optionally for the temperature conditions, during the period leading to the observation of the signals and thereafter. In fact, the type and rate of agitation and the fact that it can be reproducible are of utmost importance for the practice of this invention.

The present method affords several advantages over standard methods for the measurement of aggregation or agglutination with known aggregometers. In the present method a plurality of samples are studies at one time and are observed within the same period of time. This permits a more reliable and meaningful comparison among different the test samples, controls and/or standard curves points. Clearly, a standard curve may be run simultaneously with different concentrations of the test sample and various controls as described herein. Moreover, it is possible to average the values obtained at the same time interval for multiple simultaneously-made observations of the light transmission for similar samples and apply routine statistical analysis to produce output data such as means, standard deviations, and the like. These data can in fact be produced as curves of light transmission v. time period and/or concentration of the sample. In addition, the output from the spectrophotometer can be stored in a computer where it is readily available for analytical manipulation using standard other software packages particularly designed for this purpose.

In general, the measurement of light transmission can be undertaken at temperatures of about 15° to 45° C., preferably about 20° to 40° C. A particularly preferred temperature is about room temperature which in general may encompass a temperature of about 20° to 30° C. However, the particular embodiment where the temperature is maintained at a substantially constant value is particularly preferred in order to facilitate the comparison of data obtained for different points in time of the same sample and for different samples at the same time interval. By substantially the same or similar temperature it is understood that a variation in the temperature of up to about 2°-3° C. in most cases is acceptable. However, a lesser variation is desirable.

In the particular embodiment where the agitation of the samples is stopped immediately prior to measuring the light transmission any changes in the data produced by the absence of agitation is for all practical purposes cancelled out because all the samples are subjected to the same treatment at the same time and for the same length of time. This, therefore, eliminates any sample-to-sample variation which might be caused by the absence of agitation during the reading step.

In a preferred mode of this invention the agitation is conducted for about 5 seconds to about 1 minute and more preferably for about 7 seconds to 20 seconds, stopped for about 1 second to 1 minute, more preferably about 3 seconds to 20 seconds and thereafter restarted for a new cycle. However, variations over the above schedules are also considered part of the invention.

Having now generally described this invention, the same will be better understood by reference to certain specific examples, which are included herein for purposes of illustration only and are not intended to be limiting of the invention or any embodiment thereof, unless so specified.

EXAMPLES

EXAMPLE 1

Platelet Preparation

Platelet rich plasma (PRP) was prepared either from whole blood by methods previously described (Fratantoni, J. C., and Poindexter, B. J., Thrombosis Research 22:157-166 (1981)) or from platelets collected by automated plateletphoresis with the Fenwal CS-3000 or Haemonetics V50 devices. In all cases, the platelet count was adjusted to 300,000/uL with autologous plasma. Washed platelet suspensions were prepared from PRP and suspended in Tyrode's buffer containing albumin (Fratantoni, J. C., and Poindexter, B. J., Thrombosis Research 22:157-166 (1981)).

When platelets were stored before use, such storage was done in appropriate blood bank containers that were kept at 20°-24° C. on a horizontal flat bed agitator.

EXAMPLE 2

Aggregation Studies in Accordance with the Prior Art

Routine prior art aggregation curves were obtained with a Payton Dual Channel Aggregation Module (Payton Associates, Buffalo, N.Y.), magnetic stirrer at 1000 rpm and temperature at 37° C. unless otherwise stated.

Aggregation studies in accordance with this invention.

The cuvette holders in the Payton Aggregation Module are mounted in a heating block that can be maintained at temperatures from 34° to 41° C. Studies in the module were run either at 37° C. or with the heater off. In the latter case, a thermometer in the cuvette showed a temperature of 21° to 24° C. over a 30 minute period of stirring. The aggregation module is fitted with magnetic stirrers that were set for 1,000 rpm. The Vmax apparatus contains an agitation mechanism operates for approximately 5 seconds just prior to reading the OD. The details of this agitation (amplitude, direction, period) are proprietary and could not be obtained from the manufacturer. This agitation mechanism was not designed to maintain cells in suspension and, in fact, is not sufficient to permit platelet aggregation.

Between reading cycles, each MP was agitated for 40 to 50 seconds using a Dynatech Minishaker (CLTI, Middletown, N.Y.). This device provides a horizontal, circular motion with an amplitude of about 1.3 mm (diameter of the circle determined by each well).

The data presented here were obtained with this device at an upper level frequency setting (8 on a scale of 0 to 10, frequency=1,360 cycles/min). These specifications were obtained using a Stroboscopic Device (Strobotac, type 1531A, General Radio Co., Concord, Mass.). This agitation is critical for the present method.

EXAMPLE 3

Aggregation Studies in Accordance with this Invention

The test procedure employed a Vmax Kinetic Microplate Reader (Molecular Devices, Palo Alto, Calif.). This instrument measures the optical density at 560 mm wave length (OD560) in the 96 wells of a standard, flat-bottom MP. The OD from all wells is measured in a single operation requiring approximately 15 seconds. The OD values are processed through a microcomputer and the resultant data arrays filed on standard diskettes and stored for later processing. Measurements in the Vmax apparatus were done at room temperature.

EXAMPLE 4

Data Analysis

The stored 8×12 arrays of OD readings were converted to the format of a commercially available spreadsheet program (Lotus 1-2-3, Lotus Development Corp., Cambridge, Mass.) and the sequential time points assembled into tabular form and analyzed with standard statistical and graphic methods.

EXAMPLE 5

Method of the Invention

A layout of the MP used for a dose-response curve with ADP is shown in Table 1 below.

TABLE 1

| | | | | | Dose-Response Curve for ADP | | | | | | | |
|---|---|---|---|---|---|---|---|---|---|---|---|---|
| Wells | 1 | 2 | 3 | 4 | 5 | 6 | 7 | 8 | 9 | 10 | 11 | 12 |
| | | | | | | ADP (umolar) | | | | | | |
| 1' | B | PPP | PRP | 0.1 | 0.3 | 0.7 | 1.0 | 2.0 | 3.0 | 5.0 | 10 | 20 |
| 2' | B | PPP | PRP | 0.1 | 0.3 | 0.7 | 1.0 | 2.0 | 3.0 | 5.0 | 10 | 20 |
| 3' | B | PPP | PRP | 0.1 | 0.3 | 0.7 | 1.0 | 2.0 | 3.0 | 5.0 | 10 | 20 |
| 4' | B | PPP | PRP | 0.1 | 0.3 | 0.7 | 1.0 | 2.0 | 3.0 | 5.0 | 10 | 20 |
| 5' | B + R | PPP + R | PRP + R | 0.1 + R | 0.3 + R | 0.7 + R | 1.0 + R | 2.0 + R | 3.0 + R | 5.0 + R | 10 + R | 20 + R |
| 6' | B + R | PPP + R | PRP + R | 0.1 + R | 0.3 + R | 0.7 + R | 1.0 + R | 2.0 + R | 3.0 + R | 5.0 + R | 10 + R | 20 + R |
| 7' | B + R | PPP + R | PRP + R | 0.1 + R | 0.3 + R | 0.7 + R | 1.0 + R | 2.0 + R | 3.0 + R | 5.0 + R | 10 + R | 20 + R |
| 8' | B + R | PPP + R | PRP + R | 0.1 + R | 0.3 + R | 0.7 + R | 1.0 + R | 2.0 + R | 3.0 + R | 5.0 + R | 10 + R | 20 + R |

PPP — Platelet poor plasma.
PRP — Platelet rich plasma;
B — Buffer.
Numbers refer to final micromolar concentrations of ADP.
R — hypothetical reagent to be tested.

The agonists and other reagents were added first, and the final total volume (agonist+reagent+buffer) in all wells was the same. In this case it was 0.015 mL.

The Vmax Kinetic Microplate Reader was readied, PRP added to all wells to a final volume of 0.15 mL using a Titertek Digital Multichannel Pipette (Flow Laboratories, McLean, Va.) with 8 tips and the initial reading was taken.

Subsequent readings were taken at approximately 1 minute intervals, with agitation between readings. The agitation was conducted on a Dynatech Minishaker in a constant manner and was only stopped to take the minutes. The raw data files (8×12 arrays of OD readings) were converted to an appropriate format and the desired summary and tabular data compiled.

Readings can be done at intervals of one minute over 10 minutes. The raw data can be processed to obtain mean values for each point containing ADP with or without reagent and these are then plotted against time.

EXAMPLE 6

Comparative Platelet Aggregation Methods and the Results Obtained

Comparative studies were conducted of the present method and a prior art method utilizing a Standard Aggregometer (Payton) are shown in the Figure accompanying this patent.

In these experiments, a single platelet preparation (PRP for the ADP curves, washed platelets for the thrombin curves) was used in each pair of studies. All measurements were made at room temperature. All measurements, using both techniques, were completed within 4 hours for each pair.

The Payton device was calibrated so that the PRP sample yielded a 10% reading on the transmission scale and the PPP sample yielded a 90% reading in the same scale. This was set for each cuvette of PRP tested. The present method:

Eight replicates of each test point, including PRP or washed platelet suspension and PPP or buffer were run on the plate and optical readings were made at approximately 1 minute intervals. The exact time in seconds was recorded by the computer program.

EXAMPLE 7

Handling of Output Data

The OD values were set up in spreadsheet format and the following calculations were performed.

(1) The mean and standard deviation were calculated for each set of replicates.

(2) The mean values were corrected for blank (PPP) and expressed as percent of PRP (100%). The percent transmission was assumed to be (1-OD).

(3) Graphs were created using standard software programs.

EXAMPLE 8

Temperature Control in the Method of the Invention

The Vmax Kinetic Microplate Reader used in the method of this invention for this study is not equipped for temperature control of the MPs. Thus, all studies were performed at room temperature (21°-24° C.).

The effect of the temperature was examined using the prior art method utilizing a Payton Aggregometer. A decreased platelet reactivity at room temperature was anticipated as compared to 37° C. (Valdorf-Hansen, J. F., and Zucker, M. B., Am. J. Physiol 220:105-111 (1971)).

The results obtained when collagen was the agonist confirmed the expectations. No difference in aggregation behavior was observed though at the two temperature levels when ADP or thrombin were added as the agonists. This is shown in comparative curves presented in the figure using the full range of effective agonist concentrations (ADP: 0.1 to 10 micromolar; thrombin: 0.01 to 0.2 units/ml) on several samples of PRP or washed platelets.

Similar results were obtained with the standard aggregometer when the thermostatted cuvette holder was set at 22° or at 37°.

The electronic temperature readout on the Payton Aggregometer representative of the prior art was confirmed with a mercury thermometer in a water-filled cuvette. The mercury thermometer showed a temperature rise from 21° C. to 23° C. after 1 hour of stirring and stable reading at 37° C.

EXAMPLE 9

Agitation Speed in the Method of the Invention

The data presented here were obtained using a circular agitation frequency of about 1,360 cycles/min. A circular agitation frequency of about 1,680 cycles/min was the maximum available with the device used. This circular agitation frequency yielded aggregation curves using thrombin or ADP at multiple concentration which were not significantly different from those obtained at 1,360 cycles/min.

When the MPs were agitated at about 970 cycles/min, the rate and extent of aggregation decreased. With ADP, the maximum amplitude of irreversible aggregation was the same at both frequencies, but the time to half/maximum aggregation was 120 seconds with agitation at 130 cycles/min while it was 180 seconds with agitation at 970 cycles/min.

For reversible aggregation at low ADP concentration, the maximum amplitude with agitation at 970 cycles/min was ⅔ of that seen with circular agitation at 1,360 cycles/min. The time to maximum amplitude was 320 secs for the former and 250 secs for the latter.

The invention now being fully described, it will be apparent to one of ordinary skill in the art that many changes and modifications can be made thereto without departing from the spiritors scope of the invention herein.

We claim:

1. A rapid method for the simultaneous measurement of aggregation or agglutination of a material in a plurality of microtest wells or other sample-holding vessels, comprising providing a plurality of microtest wells or other sample-holding vessels containing a material;

providing a plurality of light beams having discrete focal points adapted to be focused on the contents of said plurality of wells or other vessels and a plurality of photodetectors therefor;

directing the light beams through the wells or other vessels and contents thereof;

continuously agitating the wells or other vessels and contents thereof with a circular movement effective to permit aggregation or agglutination while preserving the integrity of the material;

producing a plurality of output signals form the photodetectors which are proportional to the light absorbencies of the beams as they pass through the wells or other vessels and contents thereof;

repeatedly sampling the signals at a predetermined time interval; and determining changes in optical densities from the signals obtained after each predetermined time interval by comparing each signal sampled after each predetermined time interval with the first signal sampled for the same microtest well or vessel, whereby any change in optical density which is greater than about 0.05 units is said to indicate that aggregation or agglutination occurred in the well or other vessel.

2. The method of claim 1, wherein the microtest wells or other vessels contain a material which is liquid and is selected from the group consisting of a substantially light-transparent liquid medium, a liquid sample comprising an agglutinatable or aggregatable material, a liquid sample comprising an agglutinatable or aggregatable material and an agglutinating or aggregating agent, an agglutinatable or aggregatable material-rich liquid medium and an agglutinatable or aggregatable material-poor liquid medium.

3. The method of claim 2, wherein the agglutinatable or aggregatable material comprises platelets.

4. The method of claim 1, wherein at least one microtest well or other vessel contains an agglutinatable or aggregatable material-poor liquid medium;

at least one microtest well or other vessel contains a similar but agglutinatable or aggregatable material-rich liquid medium; and at least one microtest well or other vessel contains a sample further comprising an agglutinatable or aggregatable material; and said method further comprises adding to each microtest well or sample-holding vessel an agglutinating or aggregating amount of an agglutinating or aggregating agent prior to repeatedly sampling the plurality of signals at predetermined time intervals; and providing a computer and outputting into said computer the plurality of signals for each preset time and determining the optical density by further correcting each time signal for the optical density of the agglutinatable or aggregatable material-poor and material-rich media.

5. The method of claim 4, wherein the change in optical densities is calculated as percent transmission which is determined from the formula $$\% T_t = \frac{(OD_{MAt} - OD_{MPt})}{(OD_{MRt} - OD_{MPt})} \times 100$$

wherein $\% T_t$ is percent transmission of light at time t;

$OD_{MRt}$ is the optical density of the material-rich medium at time t;

$OD_{MPt}$ is the optical density of the material-poor medium at time t;

$OD_{MAt}$ is the optical density of the sample comprising the material at time t; and $OD_{At}$ is the corrected optical density of the medium comprising the material.

6. The method of claim 5, further comprising averaging the changes in optical densities for the signals obtained for microtest wells or other vessels containing the same medium for the same time interval; and averaging the changes in optical densities for the signals obtained for microtest wells or other vessels containing the same sample.

7. The method of claim 1, wherein the continuous agitation is stopped immediately before producing each plurality of output signals and is restarted immediately thereafter.

8. The method of claim 1, wherein the plurality of microtest wells or other sample-holding vessels comprise up to about 96 microtest wells or other sample-holding vessels.

9. The method of claim 1, wherein the determination of the changes in optical densities of the signals for each time interval is completed within about 1 minute.

10. The method of claim 4, further comprising diluting the medium comprising the material in a further medium to obtain a plurality of samples comprising the further medium and the material at predetermined dilutions; and wherein a plurality of microtest wells or other vessels contain such samples comprising the further medium and the material at the predetermined dilutions.

11. In a method for measuring aggregation or agglutination of a material by determining changes in optical density of the content of a sample, the improvement comprising providing a plurality of microtest wells or other sample-holding vessels containing a material;

providing a plurality of light beams having discrete focal points adapted to be focused on the contents of a plurality of wells or other vessels and a plurality of photodetectors therefor;

directing the light beams through the wells or other vessels and contents thereof;

continuously agitating the wells or other vessels and contents thereof with a circular movement effective to permit aggregation or agglutination while preserving the integrity of the material;

producing a plurality of output signals form the photodetectors which are proportional to the light absorbencies of the said beams as they pass through the wells or other vessels and contents thereof;

repeatedly sampling the signals at a predetermined time interval; and determining changes in optical densities from the signals obtained after each time interval by comparing each signal sampled after each predetermined time interval with the first signal sampled for the same microtest well or vessel, whereby each change in optical density which is greater than about 0.05 units is said to indicate that aggregation or agglutination occurred in the well or other vessel.

12. The method of claim 11, wherein the microtest wells or other vessels contain a material which is liquid and is selected from the group consisting of a substantially light-transparent liquid medium, a liquid sample comprising an agglutinatable or aggregatable material, a liquid sample comprising an agglutinatable or aggregatable material and an agglutinating or aggregating agent, an agglutinatable or aggregatable material-rich liquid medium and an agglutinatable or aggregatable material-poor liquid medium.

13. The method of claim 12, wherein the agglutinatable or aggregatable material comprises platelets.

14. The method of claim 11, wherein at least one microtest well or other vessel contains an agglutinatable or aggregatable material-poor liquid medium;

at least one microtest well or other vessel contains a similar but agglutinatable or aggregatable material-rich liquid medium; and at least one microtest well or other vessel contains a similar medium further comprising an agglutinatable or aggregatable material; and said method further comprises adding to each microtest well or sample-holding vessel an agglutinating or aggregating amount of the agglutinating or aggregating agent prior to repeatedly sampling the plurality of signals at predetermined time intervals; and providing a computer and outputting into said computer the plurality of signals for each preset time and determining the optical densities by further correcting each time signal for the optical density of the medium.

15. The method of claim 11, wherein changes in optical densities are calculated as percent transmission which is determined by subtracting the percent transmission at two different times from the formula $$\% T_t = \frac{(OD_{MA_t} - OD_{MP_t})}{(OD_{MR_t} - OD_{MP_t})} \times 100$$

wherein $\% T_t$ is percent transmission of light at time t;

$OD_{MR_t}$ is the optical density of the material rich medium at time t, $OD_{MP_t}$ is the optical density of the material poor medium at time t, $OD_{MA_t}$ is the optical density of the sample comprising the material at time t, and $OD_{A_t}$ is the corrected optical density of the medium comprising the material.

16. The method of claim 15, further comprising averaging the changes in optical density for the signals obtained for microtest wells or other vessels containing the same medium.

17. The method of claim 11, wherein the continuous agitation is stopped immediately before producing each plurality of output signals and restarted immediately thereafter.

18. The method of claim 11, wherein the plurality of microtest wells or other sample-holding vessels comprise up to about 96 microtest wells or other sample-holding vessels.

19. The method of claim 11, wherein the determination of the changes in optical densities of the signals for each time interval is completed within less than about 1 minute.

20. The method of claim 11, further comprising diluting the medium comprising the material in a medium into a plurality of samples comprising the material at predetermined dilutions; and wherein a plurality of microtest wells or other vessels contain such samples comprising the material at the predetermined dilutions.

* * * * *